US009475046B2

(12) United States Patent
Khayyami

(10) Patent No.: US 9,475,046 B2
(45) Date of Patent: Oct. 25, 2016

(54) METHOD AND DEVICE FOR IMMUNOASSAY

(75) Inventor: Masoud Khayyami, Lund (SE)

(73) Assignee: Prolight Diagnostics AB, Lund (SE)

( * ) Notice: Subject to any disclaimer, the term of this patent is extended or adjusted under 35 U.S.C. 154(b) by 797 days.

(21) Appl. No.: 12/772,449

(22) Filed: May 3, 2010

(65) Prior Publication Data

US 2011/0111438 A1    May 12, 2011

Related U.S. Application Data

(62) Division of application No. 10/289,044, filed on Nov. 6, 2002, now Pat. No. 7,709,271.

(30) Foreign Application Priority Data

Nov. 7, 2001 (SE) ....................... 0103688

(51) Int. Cl.
*G01N 33/53* (2006.01)
*B01L 3/00* (2006.01)
(Continued)

(52) U.S. Cl.
CPC ... *B01L 3/502715* (2013.01); *G01N 33/54386* (2013.01); *B01L 2200/10* (2013.01);
(Continued)

(58) Field of Classification Search
CPC ............... B01L 3/502715; B01L 2200/10; B01L 2300/025; B01L 2300/0816; B01L 2300/0819; B01L 2300/0848; B01L 2300/0858; B01L 2300/0867; B01L 2300/0883; B01L 2300/0887; B01L 2300/168; G01N 33/54386; G01N 21/6428; G01N 21/76
USPC ........................................................... 435/7.1
See application file for complete search history.

(56) References Cited

U.S. PATENT DOCUMENTS 5,313,264 A   5/1994   Ivarsson
5,485,277 A   1/1996   Foster
(Continued)

FOREIGN PATENT DOCUMENTS

EP    0671626     9/1995
JP    62169054    7/1987
(Continued)

OTHER PUBLICATIONS

Dzgoev, et al., Optimization of a charge coupled device imaging enzyme linked immuno sorbent assay and supports for the simultaneous determination of multiple 2,4-D samples, Analytica Chimica Acta 347:87-93, 1997.
(Continued)

*Primary Examiner* — Mark Shibuya
*Assistant Examiner* — Pensee Do
(74) *Attorney, Agent, or Firm* — Pierce Atwood LLP; Kevin M. Farrell; David J. Wilson

(57) ABSTRACT

The present invention relates to a method and a device for determining a concentration of a biological active substance in a sample by the means of an enzyme-linked immunosorbent assay (ELISA). The device comprises a solid support within a tubing (17) for binding an immunosorbent and an inlet (18, 19) for fluids, a detector (15) for detecting radiation due to an activity in said tubing (17), wherein said tubing (17) is arranged inside a microchip (10) extending substantially in one plane, for conducting the fluids along the plane of the microchip (10). Said tubing (17) forms a reaction cell having a large detection area (22). The reaction cell of the microchip (10) is arranged perpendicular to the detector (15).

The method comprises the steps of introducing the fluids into the tubing (17), conducting the fluids through the tubing (17) forming a reaction cell, in which reaction cell the radiation emitting activity takes place, and detecting the light emitted from the reaction cell substantially perpendicular to the plane.

24 Claims, 7 Drawing Sheets

(51) Int. Cl.
  *G01N 33/543* (2006.01)
  *G01N 21/64* (2006.01)
  *G01N 21/76* (2006.01)
  *G01N 21/03* (2006.01)

(52) U.S. Cl.
  CPC ... *B01L2300/025* (2013.01); *B01L 2300/0816* (2013.01); *B01L 2300/0819* (2013.01); *B01L 2300/0848* (2013.01); *B01L 2300/0858* (2013.01); *B01L 2300/0867* (2013.01); *B01L 2300/0883* (2013.01); *B01L 2300/0887* (2013.01); *B01L 2300/168* (2013.01); *G01N 21/6428* (2013.01); *G01N 21/76* (2013.01); *G01N 2021/0346* (2013.01)

(56) References Cited

U.S. PATENT DOCUMENTS

| | | |
|---|---|---|
| 5,624,850 A | 4/1997 | Kumar |
| 5,814,565 A | 9/1998 | Reichert |
| 6,020,209 A | 2/2000 | Narang |
| 6,046,056 A | 4/2000 | Parce |
| 6,087,102 A | 7/2000 | Chenchik |
| 6,150,180 A * | 11/2000 | Parce et al. .......... 506/7 |
| 6,222,619 B1 | 4/2001 | Herron |
| 6,306,659 B1 | 10/2001 | Parce |
| 6,686,184 B1 * | 2/2004 | Anderson et al. ........... 435/174 |
| 6,714,299 B2 | 3/2004 | Peterson |
| 6,875,619 B2 * | 4/2005 | Blackburn .......... 506/9 |
| 2002/0127740 A1 * | 9/2002 | Ho .......... 436/518 |

FOREIGN PATENT DOCUMENTS

| | | |
|---|---|---|
| WO | 99/20998 | 4/1999 |
| WO | 00/50172 | 8/2000 |

OTHER PUBLICATIONS

Momeni, et al., CCD-camera based capillary chemiluminescent detection of retinal binding protein, Analytica Chimica Acta, 387:21-27, 1999.

* cited by examiner

METHOD AND DEVICE FOR IMMUNOASSAY

TECHNICAL FIELD OF THE INVENTION

The present invention relates to a method of assaying a concentration of a substance in a sample. More precisely, the invention relates to a method for determining the concentration of a biological active substance in a sample by the means of an enzyme-linked immunosorbent assay (ELISA) performed in a tubing by detecting and quantifying radiation emitted therefrom, the radiation being proportional to the amount of the biological active substance to be assayed.

The present invention also relates to a device for determining the concentration of such a biological active substance in a sample by the means of said ELISA.

STATE OF THE ART

Light emitting reactions have been used in some immunoassays based on solid phase systems. These assays relate both quantitative and qualitative information on certain immunogenic species in a physiological sample, such as blood or urine, and employ one or more specific recognition molecules. At least one of the reacting species is attached to the solid phase, while the other is in contact with the liquid medium containing the sample. The resulting immunological complex can be used as a method for the determination of the extent of the reaction. The extent of reaction is an indication of the amount of analyte in unknown samples and can be employed in various modes.

For example, an enzyme-linked immunosorbent assay utilizes an enzyme-labelled immunoreactant (antigen or antibody) and an immunosorbent (antigen or antibody bound to a solid support). In this sensitive analytical technique an enzyme is complexed to an antigen or an antibody. Excess substances participating in the complex formation are removed by washing, and a substrate is then added generating an activity which is directly proportional to the amount of binding and thus the concentration.

This technique can be carried out in several combinations, the most used process being to coat the wells of a microtiter plate with the antigen and reacting with an antibody conjugated to a suitable enzyme, e.g. horseradish peroxidase or alkaline phosphatase. Alternatively, the wells are coated with a monoclonal antibody followed by a reaction with the antigen. The antigen is subsequently reacted with another monoclonal antibody which is conjugated with a suitable enzyme. The former case is called a direct ELISA technique while the latter is referred to as a sandwich ELISA. In yet another format the wells are coated with the antigen followed by a reaction with a monoclonal antibody which is further allowed to react with another antibody-enzyme conjugate specific to the first antibody. In such assays the enzyme acts as a tag for the measurement of the extent of the reaction. For example, the number of enzyme molecules bound to the wells is an indication of the amount of antigen present in the wells.

In JP-A-62179054 a solid phase immunoassay is shown, in which small amounts of antigen solution are determined by adsorbing antigen onto the inner wall of a polymer tube and carrying out an antigen-antibody reaction in the sample solution.

U.S. Pat. No. 5,624,850 depicts immunoassays in translucent capillary tubes, especially for detecting antibiotics in milk. A protein conjugate is used which is a hapten covalently bonded to a protein. Detection is accomplished by irradiating a specific binding pair member conjugated to a fluorescent label.

Similarly, a herbicide has been determined in a competitive immunoassay (Dzgoev et al., Analytica Chimica Acta 347 (2097) 87-93). Gold coated glass capillary tubes served as support in an imaging ELISA, bound conjugate of herbicide/bovine serum albumin being determined by the quantification of the chemiluminescence emission from the enzymatic decomposition of a luminogenic substrate. The light emitted along the entire length of the capillary tubes complicated the interpretation of the data obtained.

Although ELISA is an analytical immunochemical method with high sensitivity for measuring the concentration of all the above proteins, there is still a demand for a more sensitive method. Physiologically important substances, such as acute phase proteins, have previously been measured within a range of down to about $10^{-7}$ M, and pesticides have been detected in concentrations down to $10^{-10}$ M.

However, there are also highly sensitive methods for determining the concentration of substances, such as acute phase proteins, using an ELISA system described in the prior art. WO 9920998 discloses one such sensitive method, wherein ELISA is performed within a capillary tube from which light is emitted. The light is detected and quantified, and the detection takes place from substantially the longitudinal direction of the capillary tube.

One problem with the prior art methods and devices is that they are time consuming and expensive. A cheaper and faster assay is thus required, in which the washing procedure of for example physiological samples is simplified. It is also desired to achieve an assay system which is robust and also can be used in the field.

One drawback with methods and devices according to the prior art is that they require large fluid volumes. Subsequently, this results in poor diffusion of the fluids in the capillary tubes.

Another problem with the prior art methods and devices is the insufficient reproducibility, which affects the precision of the assay. For example, the assay results of methods using a capillary tube, from which light is emitted and the detection thereof takes place from the longitudinal direction of the capillary tube, are dependent of the distance between the fluid surface within the capillary tube and the detector. Hence, each capillary tube must be filled to exactly the same level to obtain reproducibility.

Still another problem with the prior art methods and devices is that the fluid flow is difficult to handle.

Further one drawback with methods and devices according to the prior art is that only static processes may be assayed.

SUMMARY OF THE INVENTION

One object of the present invention is to eliminate the above mentioned drawbacks and problems with prior art methods and devices for assaying a concentration of a biological active substance in a sample by the means of an ELISA. The present invention provides an efficient method and device for performing such assays within a short period of time.

The method and the device according to the invention has been developed for the assay of an unknown concentration of a substance in a sample, the substance being assayed in an assay system within a tubing by detecting and quantifying radiation, such as light, emitted from the assay system. Also other types of radiation may be used, such as radioactive radiation or the similar, which is evident for a person skilled in the art. However, light is preferably used.

The substance to be assayed can be a natural proteinous substance, or a molecule spontaneously binding to said substance. For example, the substance is a biological active substance, such as proteins, acute phase proteins, viruses, bacteria, etc. One example of acute phase proteins is myocardial infarction markers, such as FABP (Fatty Acid Binding Proteins), CK-MB, triponin-T or triponin-I, myoglobin and GPBB (Glycogene Phosphorolase iso-enzyme BB). One example of proteins is cystatin C, which may be used as a marker for renal damages. Naturally, other substances may be assayed, which is evident for a person skilled in the art.

The present invention comprises a solid support in form of a tubing serving as a reaction cell for the ELISA. The tubing is arranged in a microchip, at least a section thereof being permeable to radiation or light. The microchip extends substantially in one plane. Thus, the microchip may be a thin plate with a flat surface. The microchip may be provided with the tubing along the plane of the microchip, the tubing conducting fluids through the plane of the microchip.

The microchip may be formed in a material such as glass, plastic materials, a polymer, silicon or silicon compounds. Preferably the microchip is formed in polystyrene. The microchip may be designed light permeable or transparent in a direction towards a detector. The microchip may be designed light impermeable in a direction opposite the detector, wherein the light scattering is reduced and the light is concentrated or reflected towards the detector. Alternatively, a light reflecting layer or plate may be arranged by the microchip for reflecting the emitted light in a direction towards the detector. For example, the microchip is positioned between the detector and the light reflecting layer. The microchip may be an injection moulded article or a compression moulded article. Thus, the microchip provided with the tubing may be formed in conventional manners. Further, the tubing may be formed by milling suitable grooves in a base plate of the microchip and then providing the base plate with a cover plate, the base plate and the cover plate forming the microchip. However, this method is preferably used in small scale manufacturing of the microchips due to the rather extensive work effort required.

The microchip comprises at least one inlet for introducing fluids into the tubing and at least one outlet for the fluids. The microchip may comprise a plurality of inlets to avoid contamination. For example the microchip comprises a first inlet for proteins, a second inlet for a washing medium and further inlets, e.g. for a substrate etc. Hence, the microchip may comprise multiple inlets for introducing multiple fluids into the tubing. The fluids may be introduced into the tubing of the microchip by a conventional manner. The fluids may also be conducted through the tubing in a conventional manner, such as by the means of pressure or capillary forces. In one embodiment of the invention the fluids may be conducted by the means of a peristaltic pump. The outlet may be arranged for conducting fluids to a waste.

In an alternative embodiment of the invention the microchip may comprise reservoirs arranged within the microchip. The reservoirs may be connected with the tubing or the reaction cell by tubes for conducting fluids from the reservoirs to the reaction cell. The reservoirs may be preloaded with suitable fluids for performing the assay, which fluids can be conducted to the reaction cell in a predetermined order when the assay is initiated.

The surface of the tubing may be treated physically, such as with plasma, or chemically to improve the adsorption or covalent bonding to the surface. For example, the surface is treated with Maxisorp™ (NUNC A/S, Roskilde, Denmark) or the similar. Maxisorp™ is a polystyrene based modified surface with a high affinity for polar groups and is commonly used in connection with ELISA. Alternatively the tubing surfaces may be treated with a sol-gel type of coating. The sol-gel type of coating may be used for a microchip made of glass.

The microchip may be positioned towards a detector for detection of the light emitted from the tubing. Thus, the plane of the microchip may substantially be perpendicular in relation to the detector, wherein also the fluid flow is substantially perpendicular thereto. Thus, the light from the assay system is detected from substantially the perpendicular direction of the microchip plane according to the invention. The detector may be a photosensitive detector, such as a photocell, a photo-diode, an optical fibre, a solid state sensor (comprising an array of light sensitive cells) or a photomultiplier tube positioned at a suitable distance from the microchip. The detector may be connected to a display, a computer and a recorder in a conventional manner for processing and displaying the results obtained.

The tubing provides a large active surface area and is arranged within the microchip in a configuration obtaining a reaction cell having a large detection area as well as good fluid flow properties. The reaction cell substantially corresponds to a pad of the tubing in which the reaction takes place and the detector is detecting. In one embodiment of the invention the tubing is curved, wherein the reaction cell is arranged with a plurality of curves in the detection area. Thus, every other curve of the tubing of the reaction cell is substantially a 180° curve to the right and the remaining curves are substantially 180° curves to the left. Further, the distance between each curve is increasing in the direction from the inlet or inlets to a centre position of the reaction cell, and decreasing from the centre position of the reaction cell towards the outlet. Also other configurations of the tubing of the reaction cell are possible. In an alternative embodiment of the present invention the tubing of the reaction cell is designed as a spiral with the outlet positioned in the centre thereof. In a further embodiment of the invention the tubing may be designed with a greater width in the reaction cell area, wherein a large detection area is obtained. For example, the tubing may comprise a portion extending in the microchip plane, in which portion the fluids may be distributed for obtaining a reaction cell having a large detection area. One microchip may also comprise a plurality of tubings and a plurality of reaction cells, which makes it possible to assay and detect a substance in a number of samples simultaneously. A detector may be arranged for detecting the light emitted from each reaction cell individually or from a plurality of reaction cells in combination. Thus, the microchip may provide a multi-analytic assay system for assaying a plurality of proteins simultaneously. For example the microchip may comprise 3 or more independent reactions cells, wherein the light emitted from each reaction cell is detected.

The cross section of the tubing may be rectangular, triangular, circular, semi-circular or other suitable shape. Further, the tubing can have a depth of about 0.2 mm and a width of about 0.2 mm.

Hence, the present invention provides a reaction cell having good diffusion properties and a large detection area requiring small volumes of fluids. This results in a cheaper and faster assay, which is easy to use and wherein the fluid flow is easy to handle, which are favourable features for instruments in point-of-care. The device and method according to the invention also results in excellent assay reproducibility, which affects the precision of the assay in a positive manner. Further, the present invention makes it possible to assay dynamic processes due to the continuous fluid flow and the good diffusion. Another advantage with the present invention is the possibilities of multi-analytic assays for assaying a plurality of substances simultaneously.

In other applications the invention may also be used in assaying and detecting pathogenic substances and antioxidants in food etc.

BRIEF DESCRIPTION OF THE DRAWINGS

The invention will now be described in more detail with the aid of exemplary embodiments and with reference to the accompanying drawings, in which FIG. 1 Is a principle diagram illustrating a device set-up according to the invention.

DESCRIPTION

Figure 1:
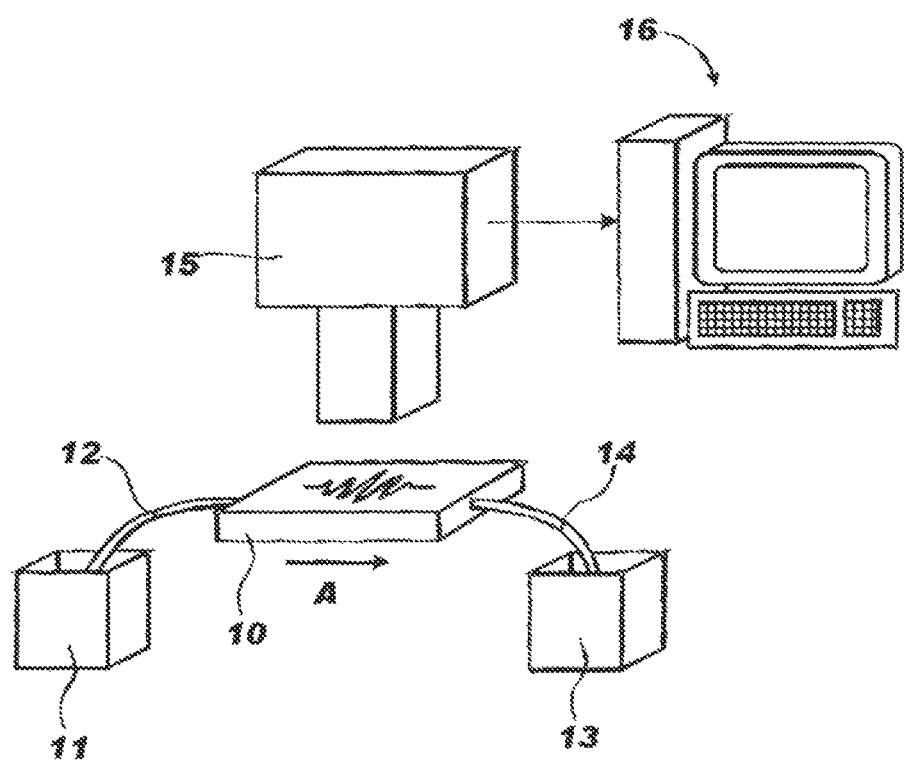

The principle diagram of FIG. 1 shows an assay device set-up for an enzyme-linked immunosorbent assay (ELISA) according to the invention. The present invention comprises a solid support for the ELISA within a radiation, or light, permeable microchip 10. The microchip 10 is designed as a thin plate with a substantially flat surface. Thus, the microchip 10 extends substantially in one plane. The microchip 10 is designed for conducting fluids through the plane of the microchip 10. For example, the fluids are conducted to the microchip 10 from at least one container 11, comprising the fluid to be introduced into the microchip 10, through at least one inlet tube 12. The fluid flow is brought through the microchip 10 and further out to a waste 13 through a waste tube 14. The principle direction of the fluid flow through the microchip 10 is indicated by the arrow A. The assay set-up may comprise a plurality of containers 11 and inlet tubes 12 for introducing fluids into the microchip 10.

The microchip 10 is positioned towards a detector 15 for detection of the light emitted from the microchip due to an ELISA related reaction. Thus, the plane of the microchip 10 is substantially perpendicular in relation to the detector 15, wherein also the fluid flow is substantially perpendicular thereto. Thus, the light from the assay system is according to the invention detected from substantially the perpendicular direction of the plane of the microchip 10. For example, the detector 15 is a photosensitive detector, such as a photocell, a photo-diode or an optical fibre, positioned at a suitable distance from the microchip 10.

In the embodiment shown in FIG. 1, the detector 15 is connected to a processing device and a display in the form of a computer 16 in a conventional manner for processing and displaying the results obtained. Additionally, the assay system may also be connected with conventional amplifiers, controllers and recorders, which are not shown in the figures, to further facilitate the processing and displaying of the results obtained.

Figure 2:
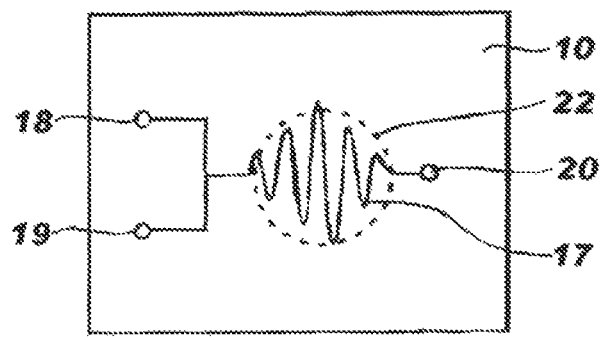
FIG. 2 is a schematic view showing the microchip perpendicular to the microchip plane according to one embodiment of the invention.
Figure 3:
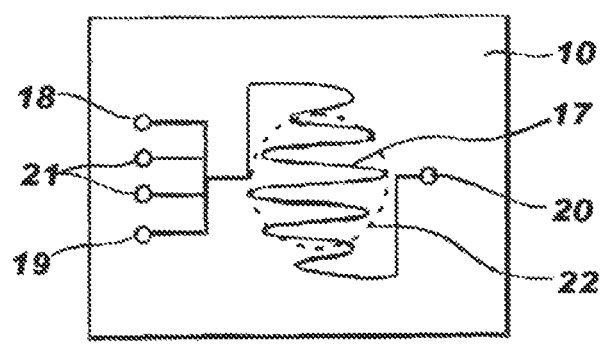
FIG. 3 is a schematic view showing the microchip perpendicular to the microchip plane according to one alternative embodiment of the invention.

With reference to FIG. 2 and FIG. 3 the microchip 10 according to the invention is shown. The microchip 10 comprises a tubing 17 arranged inside the microchip 10 for conducting fluids therein. A surface of the tubing 17 forms the solid support for the ELISA process. The microchip 10 comprises at least one inlet for introducing fluids into the tubing 17 and at least one outlet for the fluids. The microchip 10 may comprise a plurality of inlets for different fluids to avoid contamination. In the embodiment of FIG. 2, the microchip 10 comprises a first inlet 18 for introducing a first fluid into the tubing 17 within the microchip 10, a second inlet 19 for introducing a second fluid into the tubing 17 and an outlet 20 for fluids leaving the tubing 17 to the waste 13. In the embodiment of FIG. 3 the microchip 10 also comprises multiple inlets 21 for introducing further fluids, for example a washing fluid, into the tubing 17. Thus, the microchip 10 comprises multiple inlets 21 for introducing multiple fluids into the tubing 17. In the embodiments shown, the inlets 18, 19, 21 and the outlet 20 is arranged perpendicular to the plane of the microchip 10, wherein the fluids are introduced into the microchip 10 in an opposite direction to the detector 15. For example, the fluids are introduced into and conducted through the tubing 17 by the means of pressure or capillary forces. For example, the fluids are introduced into and conducted through the tubing 17 by the means of a peristaltic pump.

The tubing 17 is arranged within the microchip 10 in a configuration obtaining a reaction cell providing a large active surface area and having a large detection area 22 as well as good fluid flow properties. The detection area 22 is indicated by dashed lines in the figures. The reaction cell substantially corresponds to a part of the tubing 17 in which the ELISA related reactions take place. The tubing 17 comprises a plurality of curved sections forming a reaction cell having a large detection area 22. Preferably, the detector 15 is positioned for detection of light emitted from the reaction cell.

In the embodiments shown in FIG. 2 and FIG. 3 the tubing is curved, wherein the reaction cell is arranged with a plurality of curves in the detection area 22. Thus, every other curve of the tubing 17 of the reaction cell is substantially a 180° curve to the right and the remaining curves are substantially 180° curves to the left. Further, the distance between each curve is increasing in the direction from the first inlet 18 and the second inlet 19 to a centre position of the reaction cell, and decreasing from the centre position of the reaction cell towards the outlet 20 for obtaining a reaction cell with good fluid flow properties and a large light emitting area. The curves of the tubing 17 extends in the plane of the microchip 10.

Figure 4:
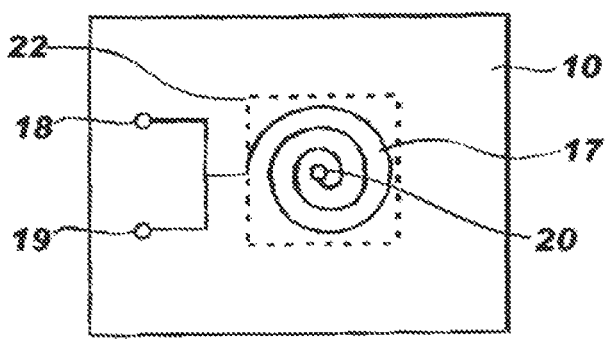
FIG. 4 is a schematic view showing the microchip perpendicular to the microchip plane according to another alternative embodiment of the invention.

With reference also to FIG. 4, showing another alternative embodiment of the tubing 17 configuration within the microchip 10, the tubing 17 is designed with curves in the form of a spiral extending in the plane of the microchip 10. In the embodiment of FIG. 4 the outlet 20 is positioned in a centre of the spiral, wherein the outlet 20 substantially is positioned in the centre of the reaction cell. However, other configurations of the tubing 17 are evident for a person skilled in the art and are within the scope of the invention.

Figure 5:
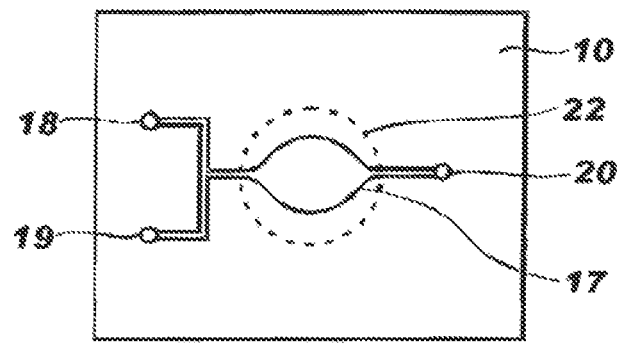
FIG. 5 is a schematic view showing the microchip perpendicular to the microchip plane according to further one alternative embodiment of the invention.

With reference to FIG. 5, the tubing 17 is designed with a greater width in the reaction cell area, wherein a large detection area 22 is obtained. In the embodiment shown in FIG. 5, the tubing 17 comprises a portion extending in the microchip plane, in which portion the fluids may be distributed for obtaining a reaction cell having a large detection area 22. For example, the width of the tubing 17 is increasing in the direction from the inlets 18, 19 to the centre of the reaction cell and decreasing from the centre of the reaction cell towards the outlet 20, obtaining a substantially circular or elliptic cavity due to the portion of the tubing 17 extending substantially in the microchip plane. Thus, the dimensions of the tubing may be varied for obtaining a suitable reaction cell having a large detection area 22. The dimension of the tubing 17 perpendicular to the microchip 17 plane may also be varied. However, other configurations of the tubing 17 are evident for a person skilled in the art and are within the scope of the invention.

Figure 6:
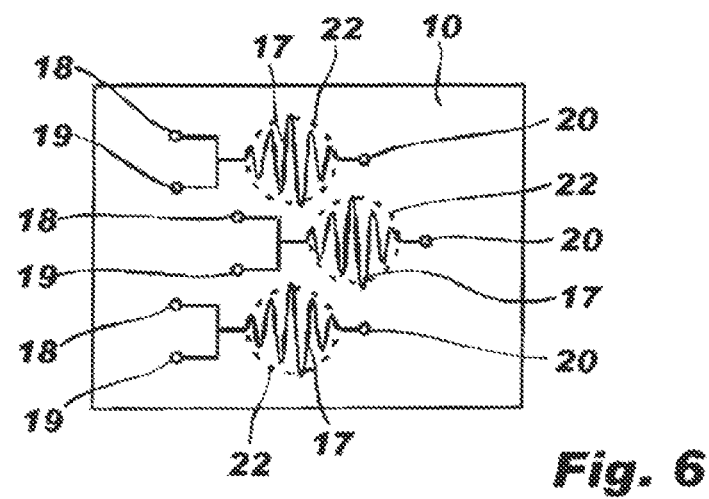
FIG. 6 is a schematic view showing the microchip perpendicular to the microchip plane according to further one alternative embodiment of the invention.
Figure 7:
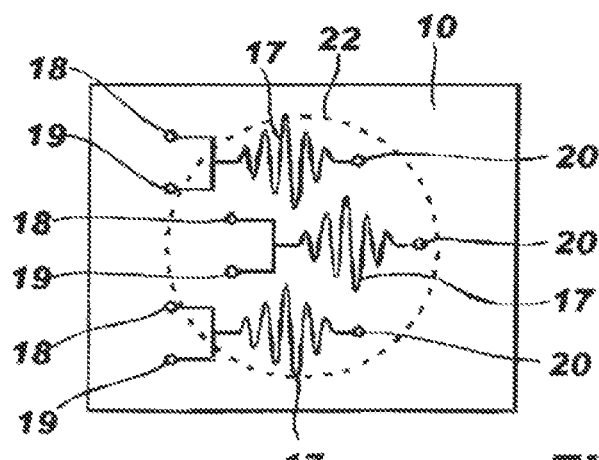
FIG. 7 is a schematic view showing the microchip perpendicular to the microchip plane according to further one alternative embodiment of the invention.

With reference to FIG. 6 and FIG. 7, one microchip 10 may also comprise a plurality of tubings 17 and a plurality of reaction cells, which makes it possible to assay and detect substances in a number of samples simultaneously. Thus, the microchip 10 may provide a multi-analytic assay system for assaying a plurality of proteins simultaneously. In the embodiment of FIG. 6, the microchip 10 comprises three independent tubings 17, wherein the inlets 18, 19 and the outlets 20 are specific for each tubing 17. Thus, the microchip 10 is arranged with a plurality of tubings 17 providing a plurality of reaction cells, wherein the light emitted from each reaction cell is detected. With reference to FIG. 6, the light emitted from each reaction cell can be detected separately, wherein each reaction cell corresponds to a separate detection area 22. With reference to FIG. 7, the light emitted from a plurality of reaction cells may be detected in combination, wherein the detection area 22 includes a plurality of reaction cells. Thus, the detector 15 covers a plurality of reaction cells simultaneously. However, other configurations and numbers of the tubings 17 are evident for a person skilled in the art and are within the scope of the invention.

Figure 8:
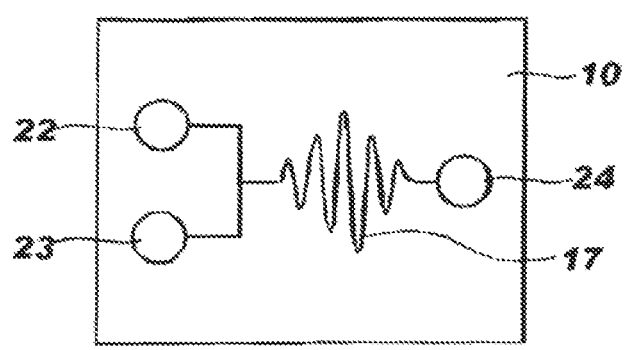
FIG. 8 is a schematic view showing the microchip perpendicular to the microchip plane according to further one alternative embodiment of the invention.

With reference to FIG. 8 the microchip 10 comprises reservoirs 22-24 arranged within the microchip 10. The reservoirs 22-24 is connected to the tubing 17, or the reaction cell, for conducting fluids from the reservoirs 22-24 to the reaction cell. In the embodiment of FIG. 8, the microchip 10 comprises a first reservoir 22 for containing a first fluid, a second reservoir 23 for containing a second fluid and a waste reservoir 23 for waste fluids. For example, the reservoirs 22, 23 are preloaded with suitable fluids for performing the assay, which fluids can be conducted to the reaction cell in a predetermined order when the assay is initiated. Examples of such fluids are buffer, washing fluids, substrate, plasma etc. The reservoirs 22-24 may replace the containers 11 and the waste 13. Other configurations and numbers of the reservoirs 22-24 are evident for a person skilled in the art and are within the scope of the invention.

Figure 9:
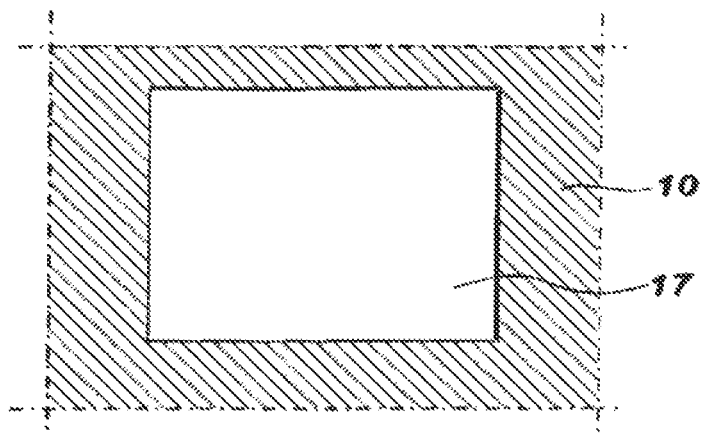
FIG. 9 is a schematic cross section view of the tubing according to one embodiment of the invention.
Figure 10:
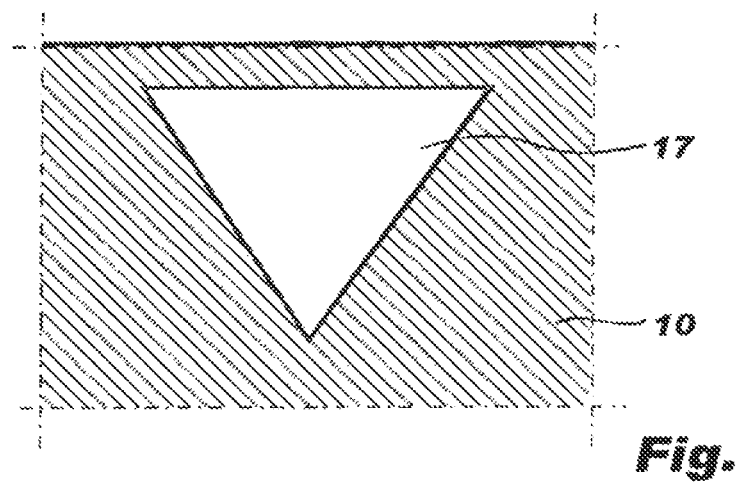
FIG. 10 is a schematic cross section view of the tubing according to an alternative embodiment of the invention.
Figure 11:
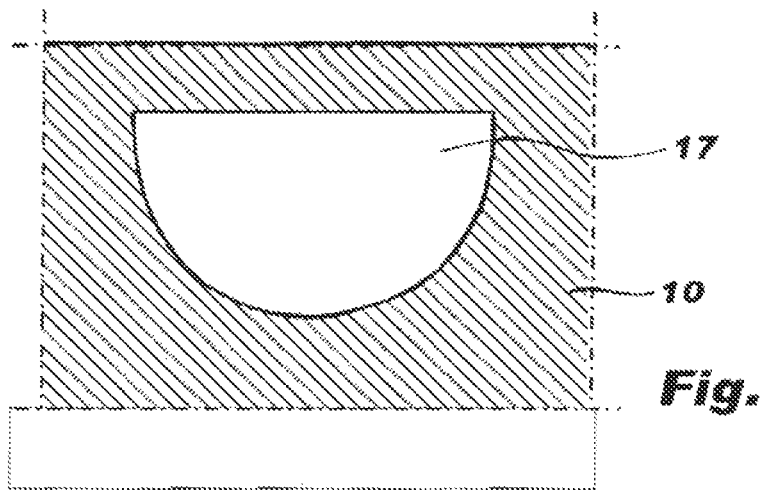
FIG. 11 is a schematic cross section view of the tubing according to another alternative embodiment of the invention.
Figure 12:
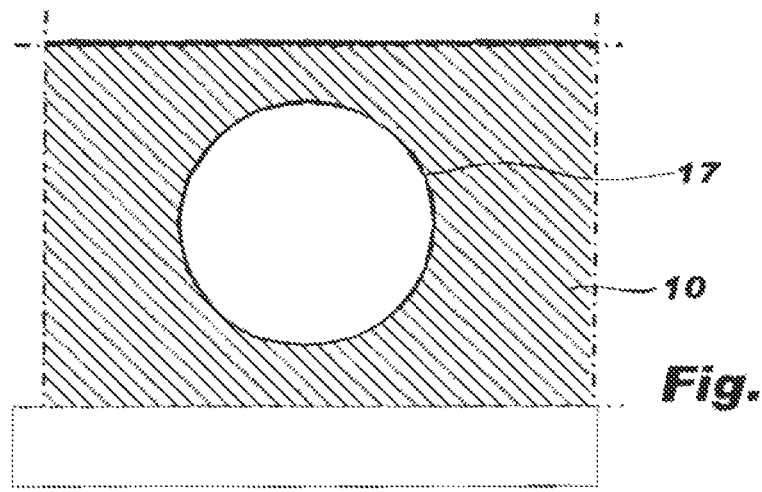
FIG. 12 is a schematic cross section view of the tubing according to further one alternative embodiment of the invention.

With reference to FIG. 9-12, showing cross section views of the tubing 17 extending in the plane of the microchip 10, the cross section of the tubing 17 may be rectangular, triangular, circular or semi-circular. In the embodiment of FIG. 9 the tubing 17 is designed with a rectangular cross section having one side directed towards the detector 15. Using triangular or semi-circular cross sections, the tubing 17 is designed for reflecting the light towards the detector 15. Thus, a flat surface of the tubing 17 is arranged in a direction towards the detector 15. In the embodiment of FIG. 10 the tubing 17 is designed with a regular triangular cross section having one side extending towards the detector 15 and an apex extending perpendicular to the plane of the microchip 10 in an opposite direction. In the embodiment of FIG. 11 the tubing 17 is designed with a semi-circular cross section having one flat side extending towards the detector 15 and an arc extending perpendicular to the plane of the microchip 10 in the opposite direction. In the embodiment of FIG. 12 the tubing 17 is designed with a circular cross section. The tubing 17 is dimensioned for good diffusion of the fluids therein. Preferably, the tubing 17 is arranged with a depth of about 0.2 mm and a width towards the detector 15 of about 0.2 mm. Other configurations of the cross section of the tubing 17 and the dimensions of the tubing 17 are evident for a person skilled in the art and are within the scope of the invention.

Figure 13:
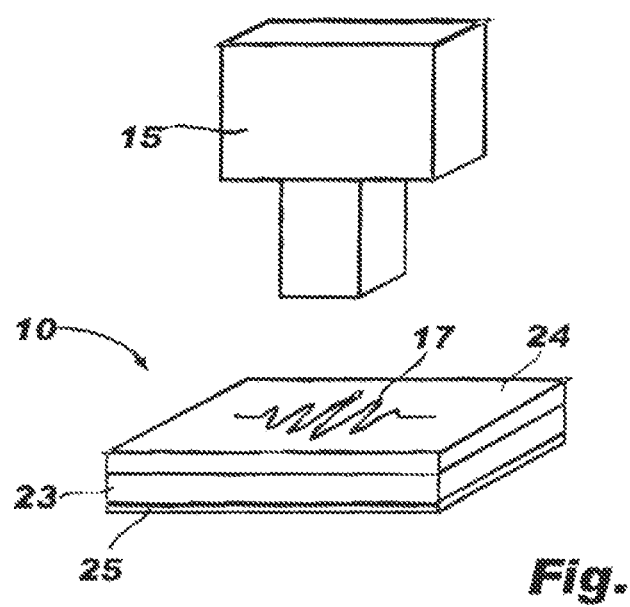
FIG. 13 is a schematic perspective view of the microchip and the detector according to further one embodiment of the invention.
Figure 14:
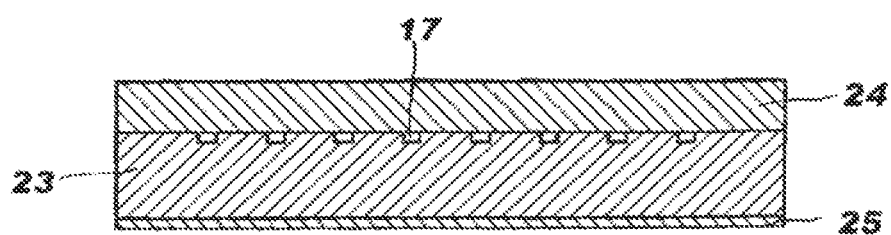
FIG. 14 is a schematic cross section view of the microchip according to the embodiment of FIG. 13.

With reference to FIG. 13 and FIG. 14 the microchip 10 according to further one embodiment is shown. The microchip 10 comprises a base plate 23 and a cover plate 24. The base plate 23 is arranged with a groove. The cover plate 24 is arranged on the base plate 23 in a direction towards the detector 15 for covering the groove, wherein the tubing 17 is formed. For example, the base plate 23 is formed in a light impermeable material or a light reflecting material and the cover plate 24 is formed in a light permeable material, wherein the light emitted from the reaction cell is directed towards the detector 15. Alternatively, a light reflecting layer 25 is provided by the microchip 10 in a direction opposite the detector 15. Thus, the light reflecting layer 25 is arranged below the microchip 10 in the figures, wherein the microchip 10 is positioned between the light reflecting layer 25 and the detector 15. The light reflecting layer 25 is designed for reflecting the light emitted from the reaction cell, wherein light scattering is reduced and the light is directed towards the detector 15.

Microchips of different materials can be used in the method according to the invention. For example, the microchips are made of glass, plastic materials, polymers, silicon, silicon compounds or similar materials. Preferably, the microchips are made of polystyrene. Preferably the material, or materials, covering the microchip towards the detector is permeable to photons produced by the assay system within the tubing. Alternatively, the reaction cell area is covered with transparent material or a material permeable to light, wherein the light emitted therefrom can be detected by the detector. A material impermeable to light may be used for the rest of the microchip, i.e. portions of the microchip directed in a direction opposite the detector, to reduce light scattering. Alternatively, the microchip is provided with a light permeable material only between the reaction cell and the detector, obtaining a "window" towards the detector.

Thus, the microchip may be arranged for concentrating the light towards the detector. For example, the microchip may be an injection moulded article or a compression moulded article. Thus, the microchip provided with the tubing can be formed in conventional manners. Alternatively, the tubing may be formed by milling suitable grooves in a base plate of the microchip and then providing the base plate with a cover plate, the base plate and the cover plate forming the microchip.

The surface of the tubing may be treated to increase the capacity thereof, i.e. increase the number of molecules or particles attached or bonded to the surface. For example, the surface is treated by physical or chemical surface treatment methods. The surface of the tubing can be treated with Maxisorp™ (NUNC A/S, Roskilde, Denmark), or the similar, prior to immobilization. Maxisorp™ is a polystyrene based modified surface with a high affinity for polar groups and is commonly used in connection with ELISA. Other examples of surface treatment are plasma treatment, treatment for increased covalent bonding to the surface of the tubing etc. For example, the tubing within a glass microchip is treated with a sol-gel type of coating. In treatment with such sol-gel the solid phase in the form of the tubing within the microchip may be pre-treated with specific reagents for removal of interfering molecules followed by silanization of the surface with silane based compounds. Especially, the nature of the silane is of specific interest due to the effects on the binding of the reagents to the solid phase support. Two separate approaches can be employed. Firstly, the treatment can be restricted to one form of silane which preferably forms a sol-gel type of coating in the tubing, and secondly mixed silanes from shorter preparation times are used to form a uniform matrix on the surface of the solid phase. For example, a continuous flow of silane solution suitable for the uniform silanization of the solid support may be introduced into the glass microchip by the means of a peristaltic pump or the similar.

One example of the silane solution for the sol-gel coating is prepared by mixing 5 ml tetramethoxysilane (TMOS), 5 ml 3-glycidylpropoxy-trimethoxysilane (GPTMOS), 90 ml deionized water, and 100 mL 0.1 M HCl. The pH of the silane solution was adjusted to 4.0 with a 10% acetic acid solution, and the solution was stirred overnight at 4° C. and 200 rpm in an airtight container for hydrolysis of the silane to yield the sol solution. The clear solution obtained was used for, the sol-gel coating process.

Another example includes activated support material for covalent coupling of a bioactive molecule via a terminal end group thereof. The functional parts on the support material (siliceous material, e.g. glass particles, colloidal silica, CPG, hydrogel, etc.) when non-activated being for hydroxyl or sulph-hydryl moieties, wherein chlorine atoms are substituted for the hydroxyl or sulph-hydryl moieties for the covalent coupling of the bioactive molecule via the terminal amino group thereof.

The light emitted is then optically screened by using the detector for photosensitive detection which is positioned at a suitable distance from the microchip, the emitted light from the microchip according to the invention being detected from substantially the perpendicular direction thereof. For example, such a light detector comprises a photodiode, a photocell, an optic fibre, a photomultiplier tube or an avalanche photodiode (APD).

By this arrangement and positioning of the microchip an excellent collection of light is obtained, and the efficiency of the assay is dramatically increased in comparison with assay methods according to the state of the art.

The assay method according to the invention is suitable for light emitted from colorimetric, fluorescent as well as chemiluminescent systems. Thus, quantitative assays can be performed which generate an emitted signal, for example from a chemiluminescence reaction, which is numerically monitored, e.g. by the means of an optical scanning mechanism having a multi-analytic capability.

Quantitative assay results can for example be obtained by using a system generating a signal from luminescence, the specific binding reagent being confined to a solid phase rather than distributed within the assay medium. This can be accomplished if the signal generated from the solid phase in the microchip is recorded by means of a light sensitive device. Thus, costly optical monitoring systems can be avoided, and the signal generated can be stored directly as a time versus intensity profile. Analytical results are especially useful in this form when a large number of samples are screened. By this set-up a substance in a sample can be assayed according to the method of the invention in concentrations as small as $10^{-19}$ M.

By using the method according to the invention robust and simple assays are provided which can be used for determining the concentration of a physiological analyte in an immunoassay. More precisely, an assay for a biological active substance in a sample is provided, the signal used in the determination of the analyte being recorded directly in a personal computer by using a suitable interface. The recorded light is derived from a light source within the microchip, the intensity of which is a measure of the analyte concentration.

Furthermore, by using the inventive method assays are provided for determining in a sample the presence of a natural protein or a molecule spontaneously binding to the same. An immunosorbent bound to the solid phase in an enzyme immunoassay can for example be an antigenic protein or an antibody to the same.

Examples of acute phase proteins of interest are FABP, CK-MB, troponin-T, troponin-I, myoglobin, GPBB and Cystatin. Other classical examples of acute phase proteins are ceruloplasmin, complement C3 and C4, orosomucoid, $a_1$-antitrypsin, $a_1$-antichymotrypsin, haptoglobin, fibrinogen, C-reactive protein, and serum amyloid A. Further examples of these proteins are the retinol-binding protein (RBP) and the mannose-binding protein (MBP). The enzyme-labelled immunoreactant can be an antibody towards the protein in question or a molecule spontaneously binding to the same.

The enzymic label is preferably involved in a luminescent reaction, most preferably in a chemiluminescent reaction. The emitted light is used as a means of determining the extent of complex formation between immunosorbent and enzyme-labelled reactant. The binding of the labelled reagent to the solid phase is then detected by the detector monitoring the chemiluminescent signal, and the electronic signal is recorded in for example a personal computer. The extent of the reaction is accordingly monitored as intensity units generated from the reaction cell within the microchip at a suitable distance therefrom.

The extent of the reaction can also be determined after the addition of an additional compounds to the assay mixture. Of particular interest are compounds which can be made to luminesce by means of photochemical, chemical, or electrochemical means. In photoluminescence the compound is induced to luminesce in a process, in which it absorbs electromagnetic radiation, for example in fluorescence or phosphorescence. In chemiluminescence a luminescent species is generated by the chemical transfer of energy to the compound in question.

When such a compound is excited into a luminescent state by chemical means a high energy derivative is obtained, e.g. by means of chemical oxidation. Upon oxidation, the chemiluminescent species emits a photon. Some compounds which can be used in luminescence-based methods, such as luminol, are not repetitive in their nature of the detectable event but produce a photon only once per molecule, and such compounds are especially suitable to use in connection with the invention. Luminol is particularly preferred as a chemiluminescent agent. However, a range of alternative compounds can be utilized, for example isoluminol, luciferin and other acridinium esters.

Thus, an effective detection system is provided for example with a label of horseradish peroxidase together with luminol and a peroxide (such as $H_2O_2$) in the reaction medium.

Generally, chemiluminescent reactions have short lifetimes and result in time constraints in the experimental procedures. This can be overcome by the use of enhancers which improve the effective duration of the light emission. Such reagents prolong the emission for a suitable period of time and enable an appropriate measurement.

Thus, by the addition of a suitable enhancer to the reaction medium, which is sufficiently chemical inert and is not to affected by the peroxide reaction, the light from the medium is provided with an appropriate wavelength which is sufficiently high to enable the enhancement in the signal after the reaction. Preferably, the enhancement of the chemiluminescent reactions is accomplished by using compounds which essentially are substituted phenols, e.g. p-iodophenol. Thus, a suitable chemiluminescent cocktail comprises a solution of 0.5 mM luminol, 0.01 mM 4-iodophenol, and 50% hydrogen peroxide.

It is advantageous to incorporate in the reaction mixture a fluorescent system which can absorb the chemiluminescent light and emit light at a different wavelength. Such a system helps to screen out the effect of light generated in the bulk sample, especially if the emitted light is viewed through an appropriate filter. For example, blue light from luminol can be absorbed by coumarin, which will emit a yellow/green light. The fluorescing agent is located on or near the signal sensing means. Alternatively, the fluorescer can be used as a marker distributed within the bulk sample so that only the locally generated chemiluminescence will be detected.

In a well designed sandwich immunoassay, which is preferred, a first specific reagent (a monoclonal antibody) with a specific reactivity for the analyte (e.g. a protein) is immobilized on the solid phase. In this connection a specific antibody means an antibody which has been selected from several similar suitable antibodies.

The assay medium, which is generally aqueous, contains a second binding reagent having a specificity for the analyte and an attached label. In the absence of analyte no coupling will occur with the first reagent and hence no detectable signal will be generated. In the sandwich configuration the analyte essentially acts as a linking molecule between the unlabelled (first) and the labelled (second) specific reagent, and the extent of coupling provides a measure of the analyte concentration in the sample.

A typical direct immunoassay is generally performed in an aqueous medium in contact with the solid phase, which contains the immobilized specific molecule (i.e. a known amount of the analyte to be assayed) having a certain specificity for the recognition molecule (i.e. a monoclonal antibody) being determined. The assay medium consists of a surplus quantity of the labelled monoclonal antibody (or analogues thereof possessing identical recognition sites) which is allowed to react with a varying quantity of the immobilized analyte, and in this way a calibration curve is obtained. The unknown quantity of the analyte is determined by immobilizing the analyte on the walls of the tubing and filling up unreacted sites of the solid phase with an inert protein (for example a gelatin fraction). The analyte is then allowed to react with the specific and labelled reagent. The extent of the reaction is determined by the signal from the labelled reagent and is monitored by using an enzymatic assay generating either a detectable emitted light. This light can for example fluorescence or chemiluminescence which is monitored by using suitable detectors. The emitted light is compared with the standard results, i.e. the results obtained in the absence of the analyte, and a measure of the analyte concentration in the sample is obtained.

In a competitive immunoassay, which is generally performed with the aqueous phase in contact with the solid phase containing the immobilized specific monoclonal antibody, the analyte is in the liquid phase. The competition takes place between labelled and unlabelled analyte. If the analyte is present in a sample, a suitable ratio of the labelled analyte is mixed with the sample and is allowed to react with the specific reagent of the immobilized solid phase. A control is obtained by the labelled analyte being allowed to react with the immobilized solid phase and is a measure of the total reaction. The presence of unlabelled analyte in the sample results in the loss of a certain percent of the signal, which is thus a measure of the unlabelled analyte in the sample. Usually, a dilution of the sample determines how the original concentration of the analyte in the sample should be calculated.

What is claimed is:

1. A method for determining the concentration of a biologically active substance in a sample by the means of a radiation emitting enzyme-linked immunosorbent assay (ELISA) performed on a solid phase within a tubing, the tubing surface forming the solid support and the tubing surface within the reaction cell forming an active surface continuously along the entire reaction cell, by detecting and quantifying the radiation emitted within the tubing, the radiation being proportional to the amount of the biological active substance assayed, by the means of a detector, comprising the steps of introducing ELISA related fluids and the sample into a microchip substantially extending in one plane, comprising the tubing, wherein said tubing encompasses a plurality of curves and wherein every other curve of the tubing is substantially a 180° curve to the right and the remaining intervening curves are substantially 180° curves to the left wherein the distance between each curve of the tubing is increasing in a direction towards a center position of the microchip and is decreasing in a direction away from the center position of the microchip to form a reaction cell, conducting the fluids through said reaction cell formed by said tubing, in which reaction cell the radiation emitting activity takes place, and detecting the light emitted from the reaction cell substantially perpendicular to the plane in which the curves extend, wherein detection of the light emitted from the reaction cell is proportional to the concentration of the biologically active substance.

2. A method according to claim 1, further including the step of introducing a first fluid into the tubing through a first inlet and introducing a second fluid into the tubing through a second inlet to avoid contamination.

3. A method according to claim 1, further including the step of conducting the fluids to a waste reservoir through an outlet.

4. A method according to claim 1, further including the step of introducing multiple fluids into the tubing through multiple inlets.

5. A method according to claim 1, further including the step of detecting the light emitted from the reaction cell by the means of a photodiode, photocell, optic fibre, solid state sensor or a photomultiplier tube.

6. A method according to claim 1, further including the step of conducting the fluids through a plurality of curves of said tubing.

7. A method according to claim 1, further including the step of conducting fluids to a plurality of separately arranged reaction cells for assaying a plurality of substances simultaneously.

8. A method according to claim 7, further including the step of assaying various biological substances.

9. A method according to claim 8, further including the step of assaying acute phase proteins.

10. A method according to claim 9, further including the step of assaying infarction markers.

11. A method according to claim 7, further including the step of detecting the light emitted from each reaction cell separately.

12. A method according to claim 7, further including the step of detecting the light emitted from a plurality of reaction cells in combination.

13. A method for determining the concentration of a biologically active substance in a sample by the means of a radiation emitting enzyme-linked immunosorbent assay (ELISA) performed on a solid phase within a tubing, the tubing surface forming the solid support and the tubing surface within the reaction cell forming an active surface continuously along the entire reaction cell, by detecting and quantifying the radiation emitted within the tubing, the radiation being proportional to the amount of the biological active substance assayed, by the means of a detector, comprising the steps of introducing ELISA related fluids and the sample into a microchip substantially extending in one plane, comprising the tubing, wherein said tubing encompasses a plurality of curves, the plurality of curves forming a spiral having said outlet at the center position of the microchip to form a reaction cell, conducting the fluids through said reaction cell, in which reaction cell formed by said tubing the radiation emitting activity takes place, and detecting the light emitted from the reaction cell substantially perpendicular to the plane in which the curves extend, wherein detection of the light emitted from the reaction cell is proportional to the concentration of the biologically active substance.

14. A method according to claim 13, further including the step of introducing a first fluid into the tubing through a first inlet and introducing a second fluid into the tubing through a second inlet to avoid contamination.

15. A method according to claim 13, further including the step of conducting the fluids to a waste reservoir through an outlet.

16. A method according to claim 13, further including the step of introducing multiple fluids into the tubing through multiple inlets.

17. A method according to claim 13, further including the step of detecting the light emitted from the reaction cell by the means of a photodiode, photocell, optic fibre, solid state sensor or a photomultiplier tube.

18. A method according to claim 13, further including the step of conducting the fluids through a plurality of curves of said tubing.

19. A method according to claim 13, further including the step of conducting fluids to a plurality of separately arranged reaction cells for assaying a plurality of substances simultaneously.

20. A method according to claim 19, further including the step of assaying various biological substances.

21. A method according to claim 20, further including the step of assaying acute phase proteins.

22. A method according to claim 21, further including the step of assaying infarction markers.

23. A method according to claim 19, further including the step of detecting the light emitted from each reaction cell separately.

24. A method according to claim 19, further including the step of detecting the light emitted from a plurality of reaction cells in combination.

* * * * *